(12) United States Patent
Hamidian Jahromi et al.

(10) Patent No.: US 10,137,293 B2
(45) Date of Patent: Nov. 27, 2018

(54) MEDICAL STOPCOCK VALVE

(71) Applicant: BOARD OF SUPERVISORS OF LOUISIANA STATE UNIVERSITY AND AGRICULTURAL AND MECHANICAL COLLEGE, ACTING THROUGH THE LOUISIANA STATE UNIVERSITY SCIENCES CENTER, Baton Rouge, LA (US)

(72) Inventors: Alireza Hamidian Jahromi, Shreveport, LA (US); David Hilton Ballard, Shreveport, LA (US); Jeffery Adam Weisman, West Monroe, LA (US); Horacio Ruben Vincent D'Agostino, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 15/113,929

(22) PCT Filed: Jan. 23, 2015

(86) PCT No.: PCT/US2015/012593
§ 371 (c)(1),
(2) Date: Jul. 25, 2016

(87) PCT Pub. No.: WO2015/112803
PCT Pub. Date: Jul. 30, 2015

(65) Prior Publication Data
US 2016/0339228 A1    Nov. 24, 2016

Related U.S. Application Data

(60) Provisional application No. 61/931,610, filed on Jan. 25, 2014.

(51) Int. Cl.
*A61M 5/00* (2006.01)
*A61M 39/22* (2006.01)

(52) U.S. Cl.
CPC ..... *A61M 39/223* (2013.01); *A61M 2039/229* (2013.01); *A61M 2205/581* (2013.01); *A61M 2205/582* (2013.01)

(58) Field of Classification Search
CPC ...... A61M 2039/229; A61M 2205/581; A61M 2205/582; A61M 39/223
(Continued)

(56) References Cited

U.S. PATENT DOCUMENTS

| 4,207,923 A | * | 6/1980 | Giurtino | ............. | A61M 39/223 |
| | | | | | 137/625.47 |
| 4,865,583 A | | 9/1989 | Tu | | |
| 5,144,972 A | | 9/1992 | Dryden | | |
| 5,839,470 A | * | 11/1998 | Hiejima | ............. | A61M 5/16877 |
| | | | | | 137/599.08 |

(Continued)

FOREIGN PATENT DOCUMENTS

| ES | 1 063 415 U | 10/2006 |
| JP | 2012-183099 A | 9/2012 |
| RU | 2 230 964 C2 | 6/2004 |

OTHER PUBLICATIONS

International Search Report Corresponding to PCT/US2015/012593 dated May 4, 2015.
(Continued)

*Primary Examiner* — Jason Flick
(74) *Attorney, Agent, or Firm* — Davis & Bujold, PLLC

(57) ABSTRACT

A medical stopcock which allows easier switching operation of plural branch-tubes. The main body of the stopcock comprises a chamber part with a nearly spherical inner surface, and an upstream branch-tube, a downstream branch-tube and a merge-branch-tube all extending from the chamber part. A valve body of the stopcock comprises a nearly spherical valve main body and a rod-shaped operating part
(Continued)

Opposite sides open with a guide hole linking the inner surface of the chamber part to the outside. In operation, the rod-shaped operating part is moved along the guide hole through the use of the horizontal flow passages and the vertical flow passage to allow the predetermined branch-tubes out of the upstream branch-tube, the downstream branch-tube and the merge-branch-tube to communicate with one another or to shut-off the communication.

15 Claims, 20 Drawing Sheets

(58) Field of Classification Search
USPC .......................................................... 604/248
See application file for complete search history.

(56) References Cited

U.S. PATENT DOCUMENTS

| | | |
|---|---|---|
| 7,165,568 B2 * | 1/2007 | Kessell .............. A47G 19/2266 137/68.19 |
| 7,232,428 B1 | 6/2007 | Inukai et al. |
| 8,317,758 B2 | 11/2012 | Funamura et al. |
| 8,534,321 B2 | 9/2013 | Ziv et al. |
| 8,584,701 B2 | 11/2013 | Duncan |

OTHER PUBLICATIONS

Written Opinion Corresponding to PCT/US2015/012593 dated May 4, 2015.

* cited by examiner all 3 open all closed

Two open (bottom and right)

all closed

Opposite sides open all closed

Two open (bottom and left)

all closed

MEDICAL STOPCOCK VALVE

BACKGROUND OF THE INVENTION

Field of the Background

The present invention relates to stopcocks generally, and more specifically to medical stopcocks. It also relates to fluid control devices in general and in particular to fluid control devices adapted for facilitating the aseptic administration of drugs to patients.

Description of the Background

Modern medicine requires nearly universal intravenous access and catheter usage among hospital patients. The tubing required for drug delivery must have flow rates be controlled by precise valves or stopcocks. Three-way stopcocks are known as one type of such medical instruments for fluid control. A 3-way stopcock includes three tributary tubes that are separated from one another by an angle of, for example, 90°.

The conventional 3-way stopcock is arranged between a patient and a source of infusion fluid so that when the valve body is turned, the flow of infusion fluid is selectively switched from one flow passage to another. The most common arrangement for the flows are in the shape of a "T." In this arrangement if there is a primary input at 0° then the primary output is going to be at opposite location at 180°. The third port that acts as a tributary for flow is at 90° and can be an input or output for the flow of fluid.

It is important to note that the number of tributaries in a stopcock valve can be as low as two but also be substantially higher. There are several valves in the literature with a plurality of tributaries. The only limiting factor is the size of the tributaries or the spacing of them to allow for the valve to be selectively closed. One of the limiting factors in such cases is the cumulative size of the tributaries or the total space allocated to the valve chamber to allow for the tributaries to be selectively closed. Allowing flow to not narrow or only expand or pool is an important consideration in stopcock design.

While the tributary input and output tubes are in communication with each other for administration of a drug solution, there is a third tube, not in use, which is left unattended. Accordingly, there is a risk of microbial contamination from the end region of the tributary tube. Also, there is a concern that the drug solution, or drainage fluid, remaining within the tributary tube, which radially extends away from the main body, provides an ideal breeding ground for bacteria and other microorganisms.

Stopcocks are widely used to direct the flow of multiple compatible intravenous (IV) solutions into one IV line. A stopcock allows the user increased flexibility to select from several input lines and various combinations of the above to run into the output line or to stop the IV flow altogether. It is advantageous to run multiple lines into one line because this can dilute out a particular drug that is irritating to patients and it can also decrease the need for multiple IV sites in a patient.

While IV stopcocks are widely, used because of their advantages, they have several disadvantages. It is difficult to handle current stopcocks without touch contamination because of their small size with short connector arms that are unprotected from touch contamination. Another disadvantage of the current stopcocks is because of the short handle lengths on the rotors that are turned to select the flow desired through the stopcocks. A further disadvantage is the small internal fluid passageways that restrict the flow of viscous fluids, especially blood. This can substantially increase the time it takes to infuse these fluids Because of this, it may be necessary to utilize pumps to force the fluids through these restricted passageways. It is frequently necessary to push IV drugs through injection ports while the stopcock is in place. Therefore, lack of an injection port on commercially available stopcocks may cause inconvenience or require additional IV lines to be placed in the patient. The placement of additional lines may cause the patient discomfort and may be difficult for healthcare workers because of the patient's physiological condition. Most stopcocks are of limited input capacity and have only two input arms and one output arm. This is frequently insufficient; so multiple stopcocks are required in combination to supply sufficient input line capacity.

Small internal fluid passageway's in the current stopcock designs and subsequent restriction of the flow have other consequences. In case the stopcock is used for the viscous fluids, blood and body fluids, the stopcocks especially in their current designs, are extremely prone to get occluded by the debris and the clotted material such as blood clots.

To prevent bacterial infection from an unused tributary several stopcocks institute a continuous flow path. The primary tributary makes a "u turn" or conducts a flow pattern in the shape of a horseshoe. One problem with this "u turn" approach is that the tributary narrows to a fraction of the width at the primary entry and exit points. This can allow for clogging or a slowing of the flow.

The current level of medical stopcock technology only has a single "off position." If the lever is not in the precise off position there may still be some flow. Conversely, if the lever is not perfectly in the on positions the flow may be constricted.

In addition to the issues of infection and valve dogging there is a lesser-mentioned design flaw in medical stopcocks. They cause skin ulcers or lesions frequently in bed-bound patients. The pointed edges of the hard plastics will cause abrasions on the skin of patients who put weight on the devices. There is a need for alternative designs that do not cause skin damage or discomfort to patients.

Additional background on medical stopcocks can be found within US Patents and the references they incorporate, numbered but not limited to: U.S. Pat. No. 8,584,701 B2, U.S. Pat. No. 8,534,321 B2, U.S. Pat. No. 8,317,758 B2, U.S. Pat. No. 7,232,428 B1, U.S. Pat. No. 5,144,972 A and U.S. Pat. No. 4,865,583 A.

The literature shows a clear need for a better designed medical stopcock.

BRIEF DESCRIPTION OF THE DRAWINGS

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which.

DETAILED DESCRIPTION OF THE INVENTION

Figure 1:
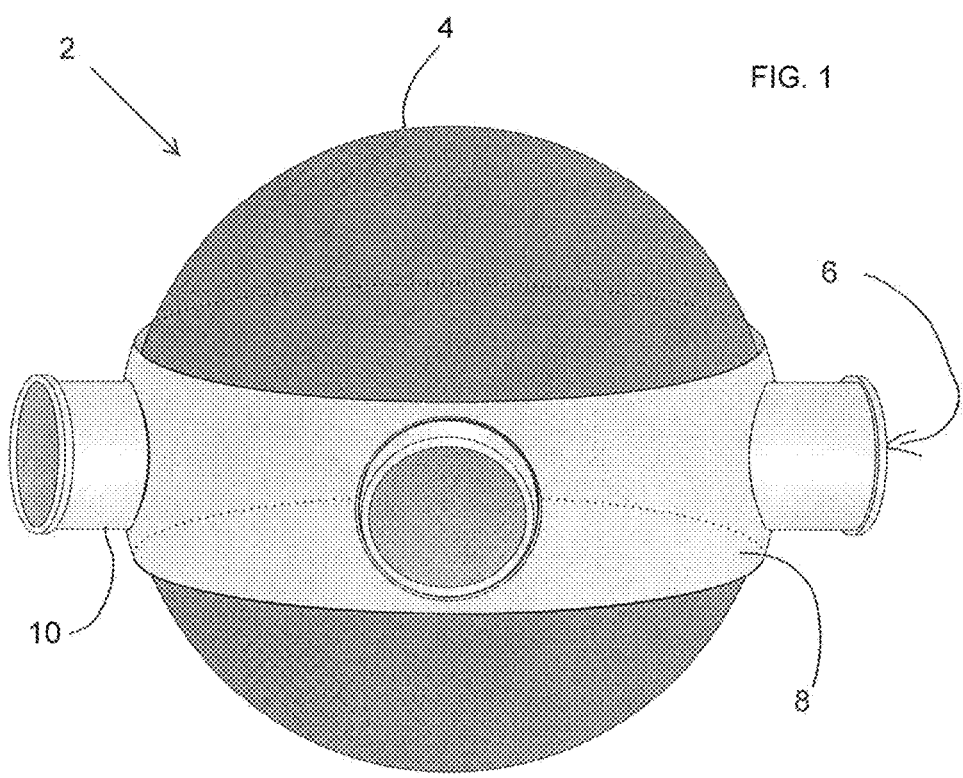
FIG. 1 is a partial see-through diagrammatic front view of a first embodiment of a medical stopcock according to the invention.
Figure 2:
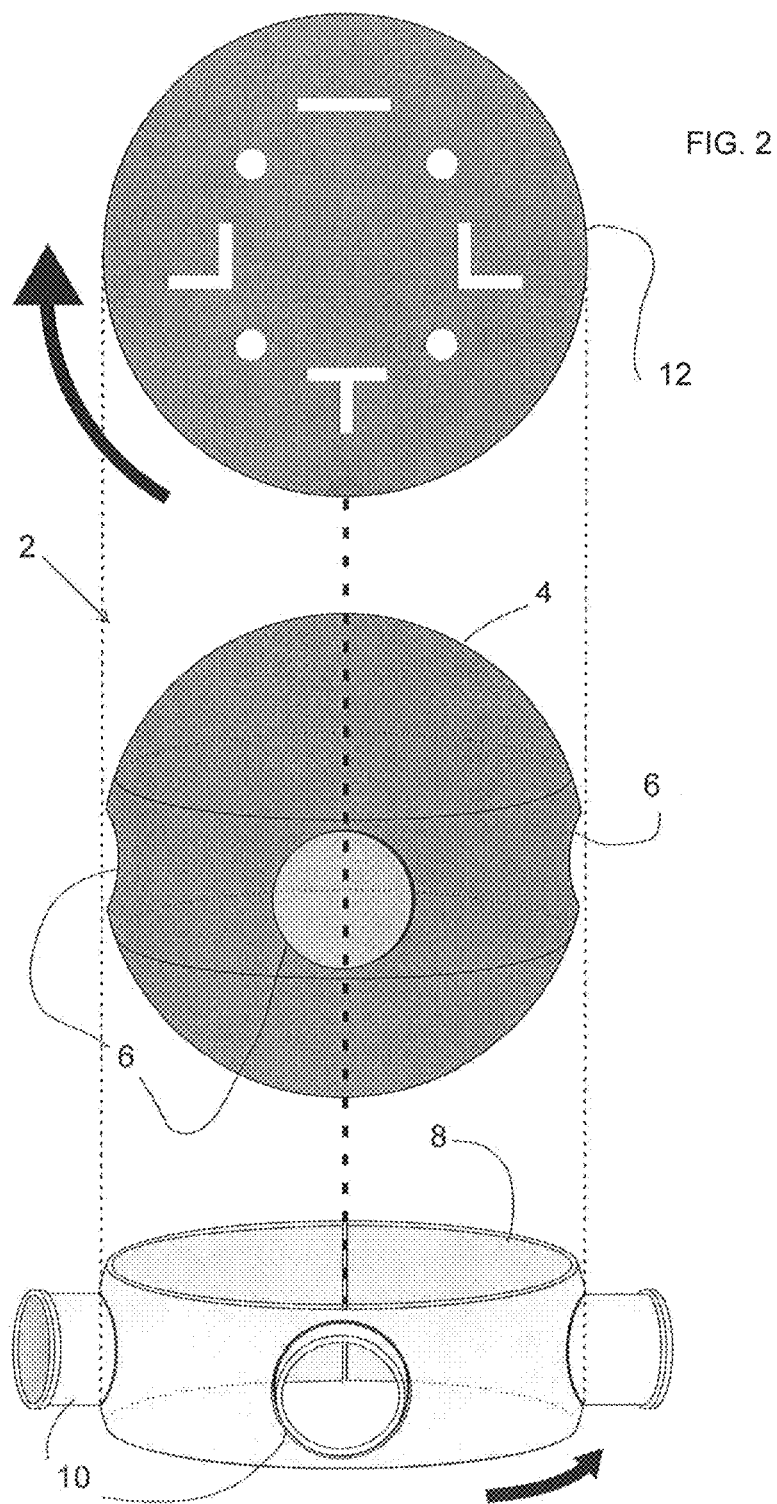
FIG. 2 is a an exploded view of the medical stopcock of FIG. 1 in a first stable open position where all there external ports on the outer collar are aligned with a respective through hole in the hollow sphere.
Figure 3:
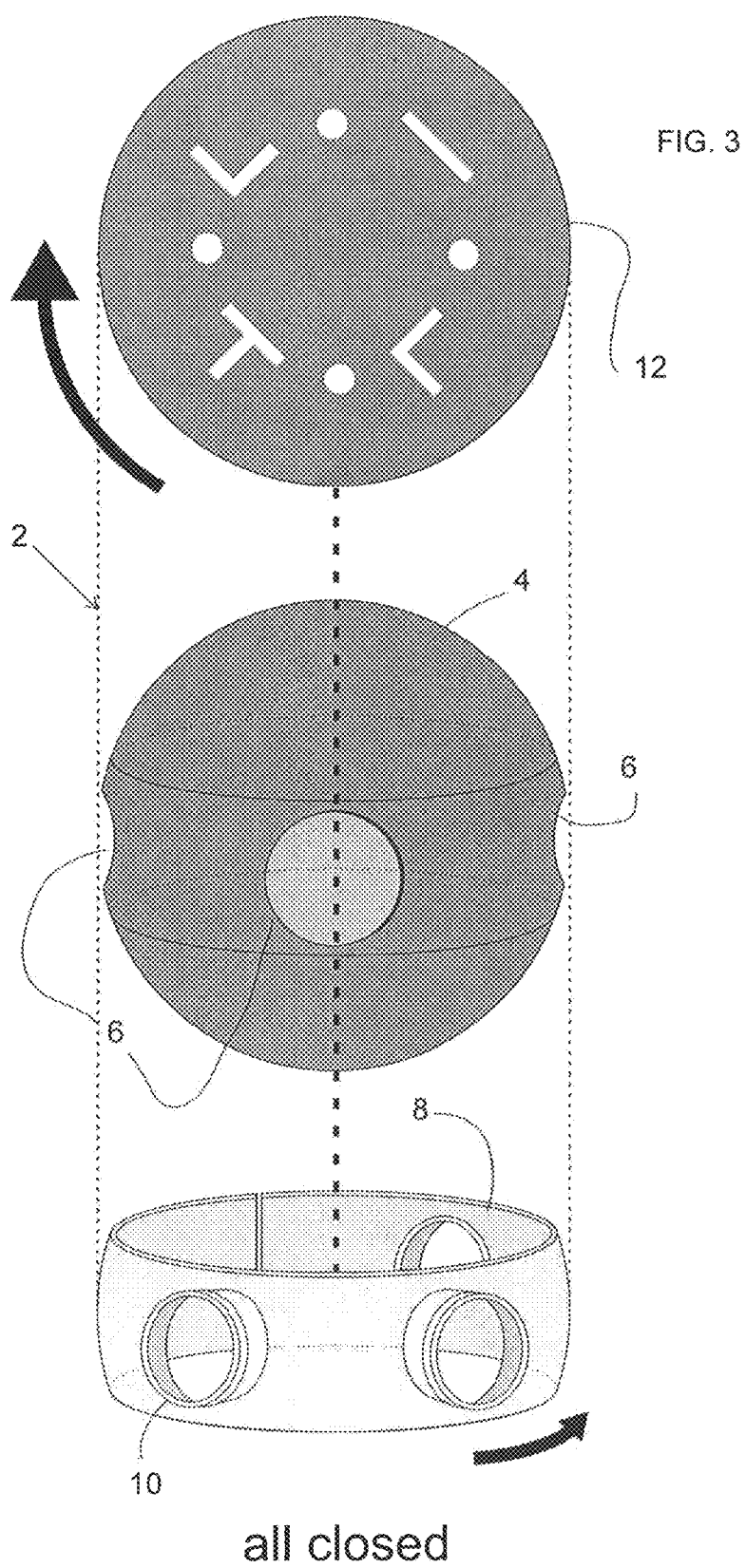
FIG. 3 is a an exploded view of the medical stopcock of FIG. 1 in a first stable closed position, 45 degrees from the first stable open position, where all there external ports on the outer collar are closed off from all of the are through holes in the hollow sphere.
Figure 4:
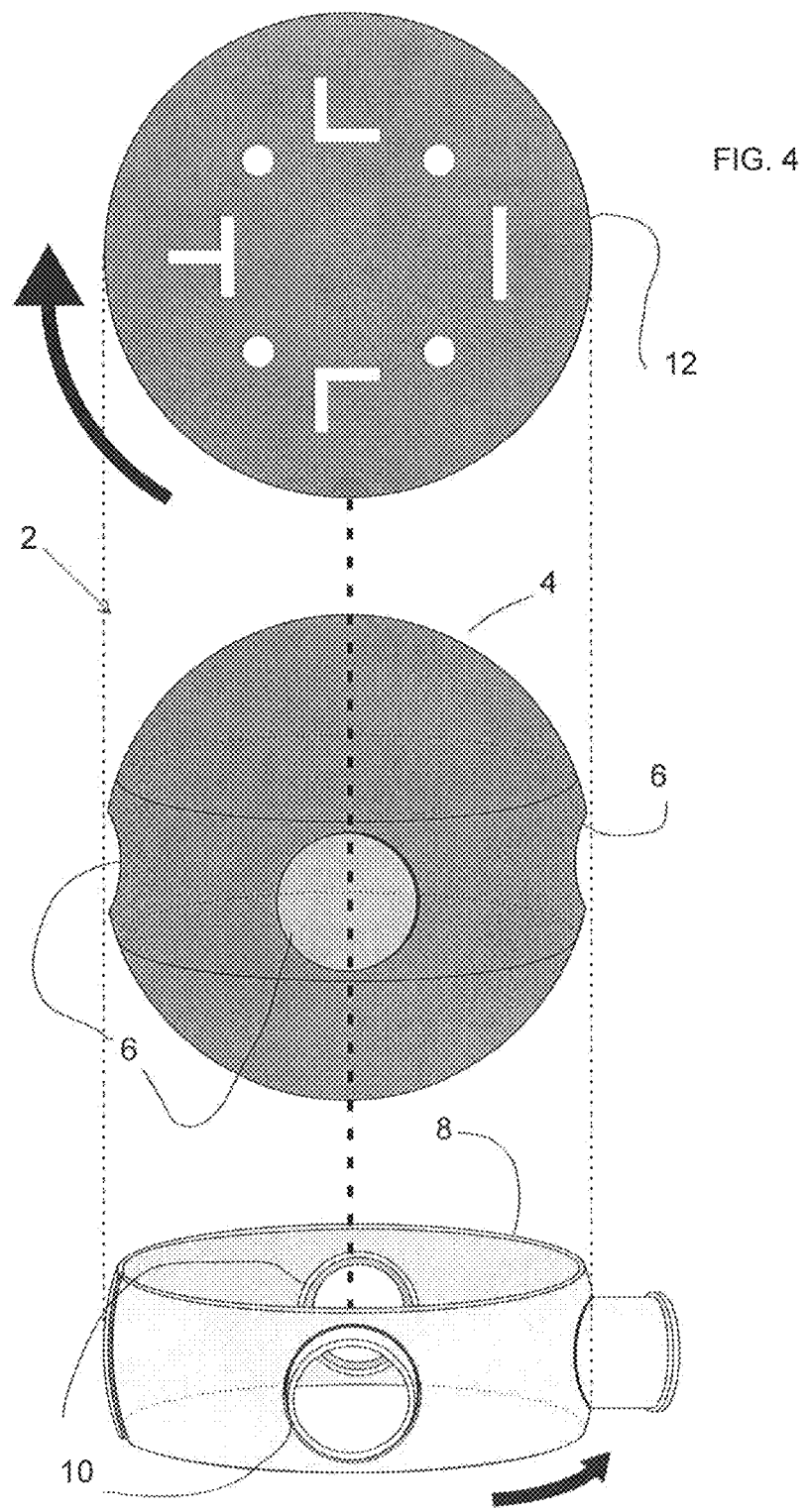
FIG. 4 is a an exploded view of the medical stopcock of FIG. 1 in a second stable open position, 90 degrees from the first stable open position, where the front and the right side through holes in the hollow sphere are aligned with a respective external port on the outer collar, and the left side through hole in the hollow sphere is aligned with a solid surface of the collar, and thus fluidly closed, and a third external port is aligned with a solid surface of the back of the hollow sphere, and thus fluidly closed.
Figure 5:
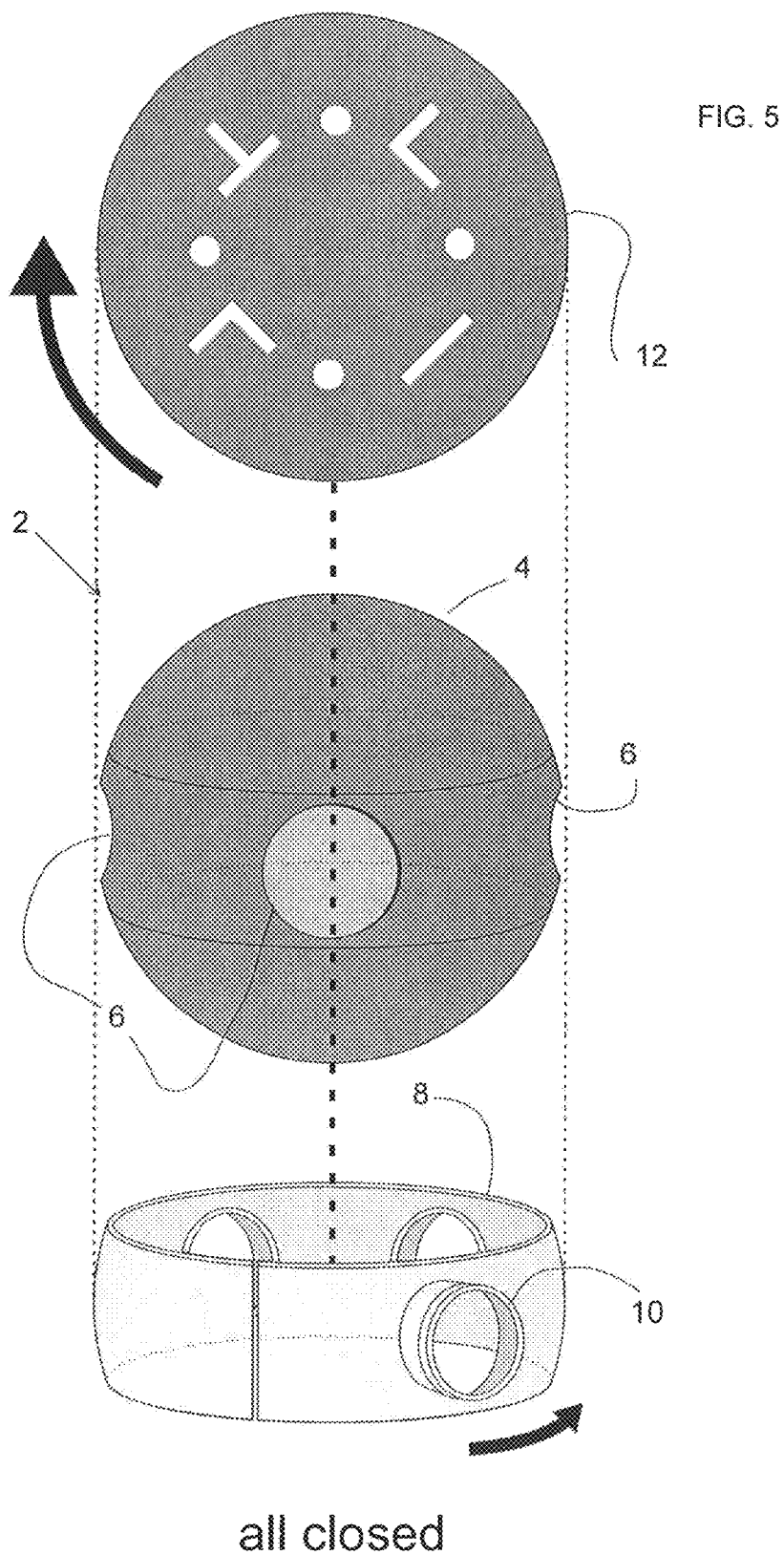
FIG. 5 is an exploded view of the medical stopcock of FIG. 1 in a second stable closed position, 90 degrees from the first stable closed position and 45 degrees from the second stable open position, where all there external ports on the outer collar are closed off from all of the through holes in the hollow sphere.
Figure 6:
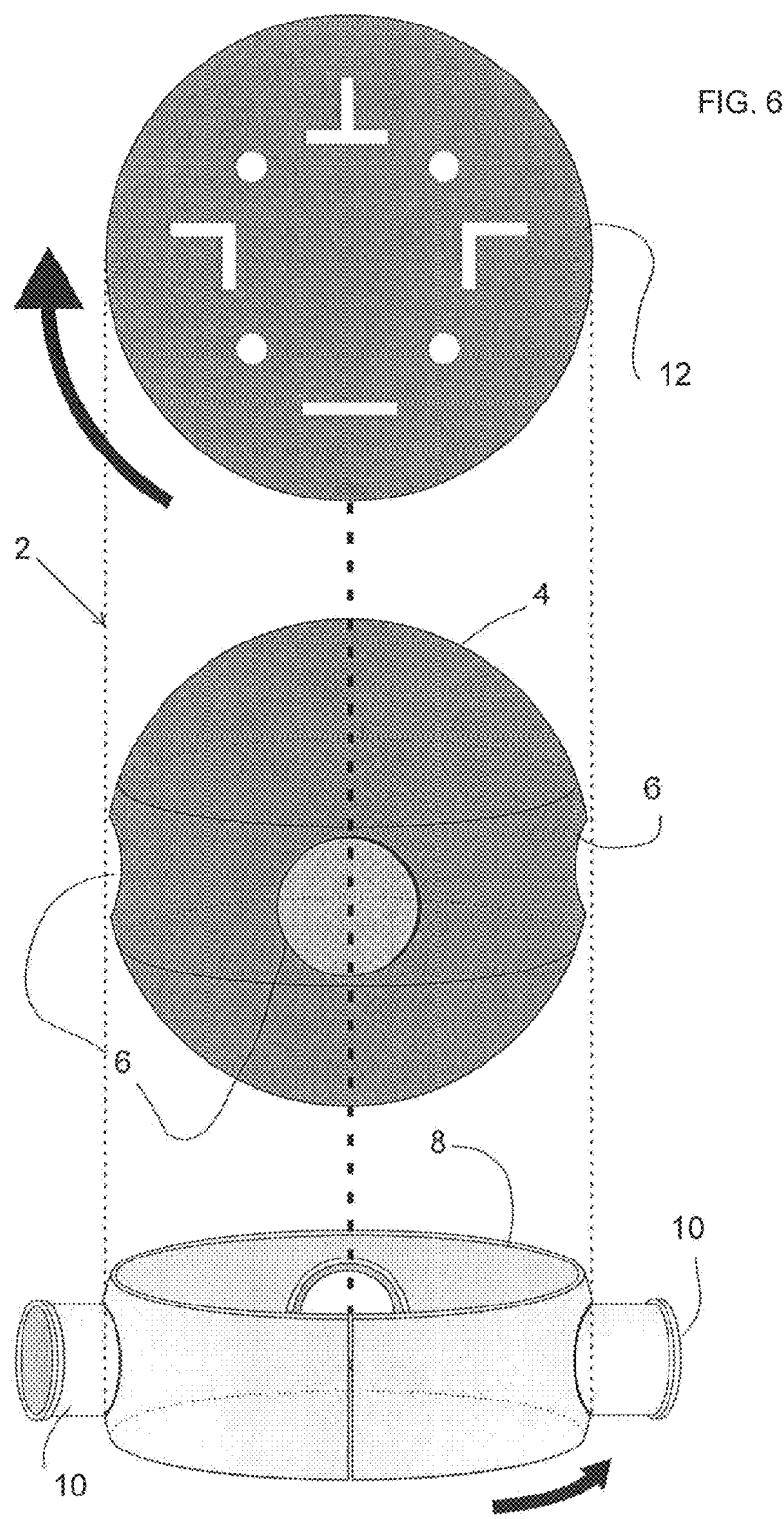
FIG. 6 is a an exploded view of the medical stopcock of FIG. 1 in a third stable open position, 90 degrees from the second stable open position, where the left side and the right side through holes in the hollow sphere are aligned with a respective external port on the outer collar, and the front through hole in the hollow sphere is aligned with a solid surface of the collar, and thus fluidly closed, and a third external port is aligned with a solid surface of the back of the hollow sphere, and thus fluidly closed.
Figure 7:
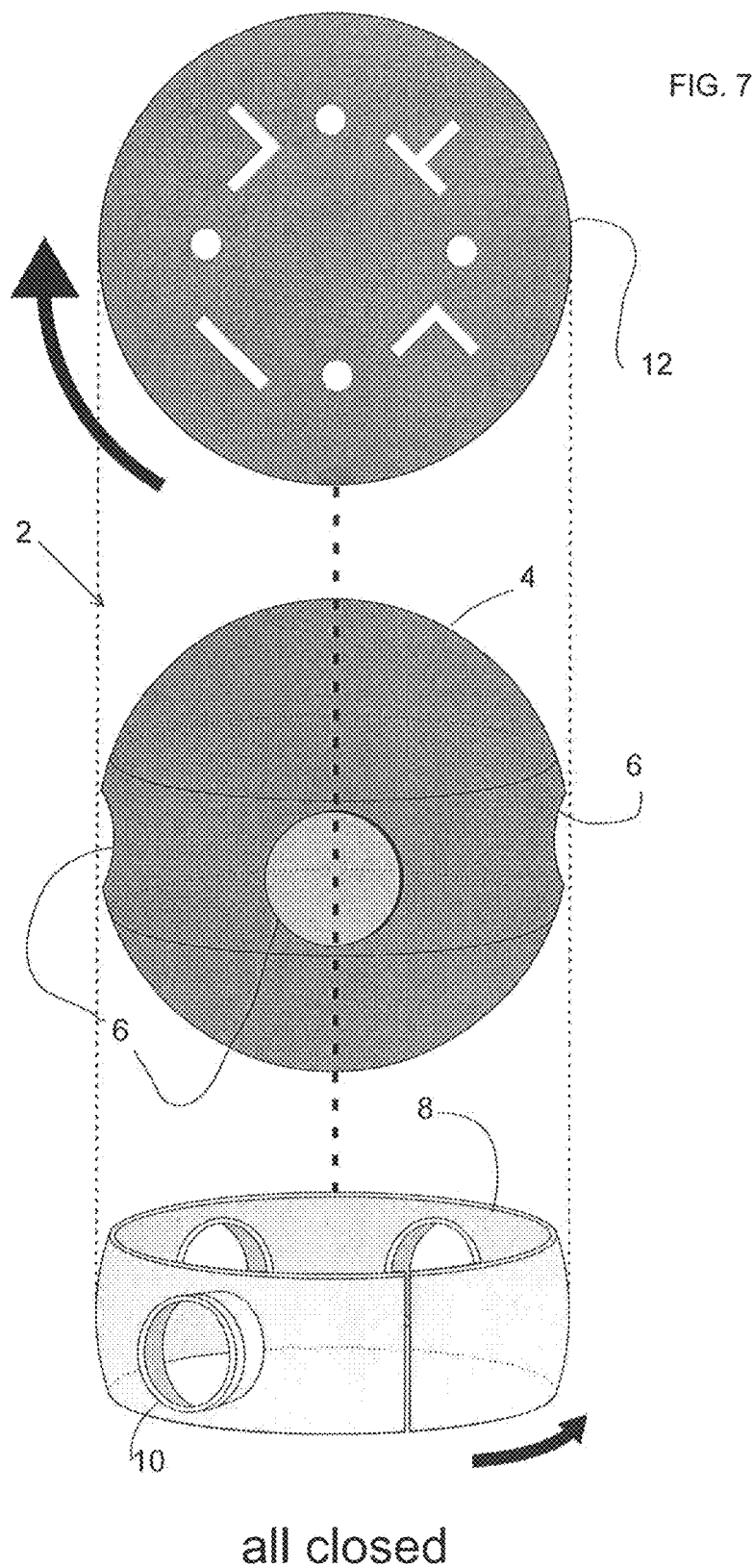
FIG. 7 is an exploded view of the medical stopcock of FIG. 1 in a third stable closed position, 90 degrees from the second stable closed position and 45 degrees from the third stable open position, where all there external ports on the outer collar are closed off from all of the through holes in the hollow sphere.
Figure 8:
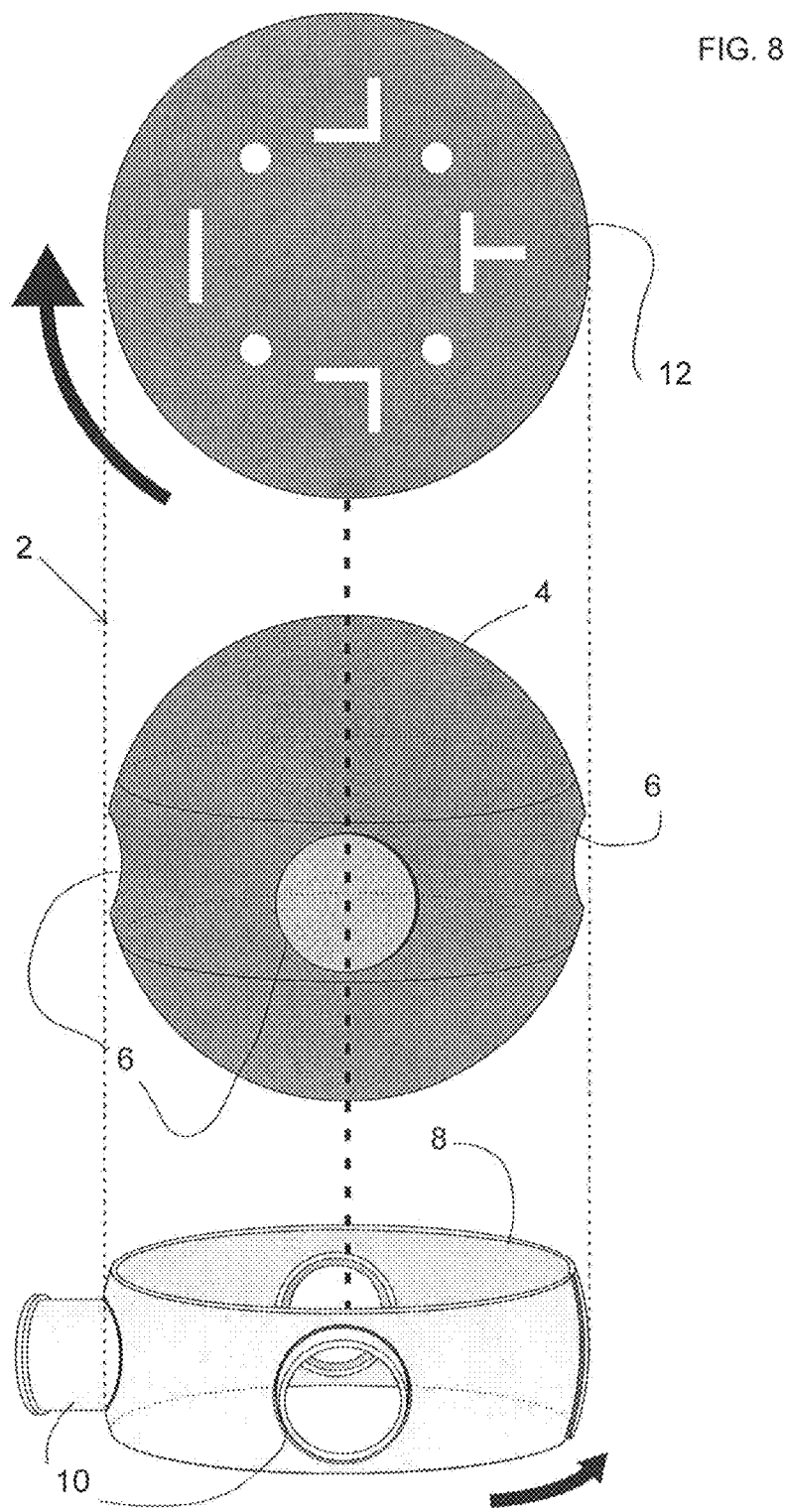
FIG. 8 is an exploded view of the medical stopcock of FIG. 1 in a fourth stable open position, 90 degrees from the third stable open position, where the front and the left side through holes in the hollow sphere are aligned with a respective external port on the outer collar, and the right side through hole in the hollow sphere is aligned with a solid surface of the collar, and thus fluidly closed, and a third external port is aligned with a solid surface of the back of the hollow sphere, and thus fluidly closed.
Figure 9:
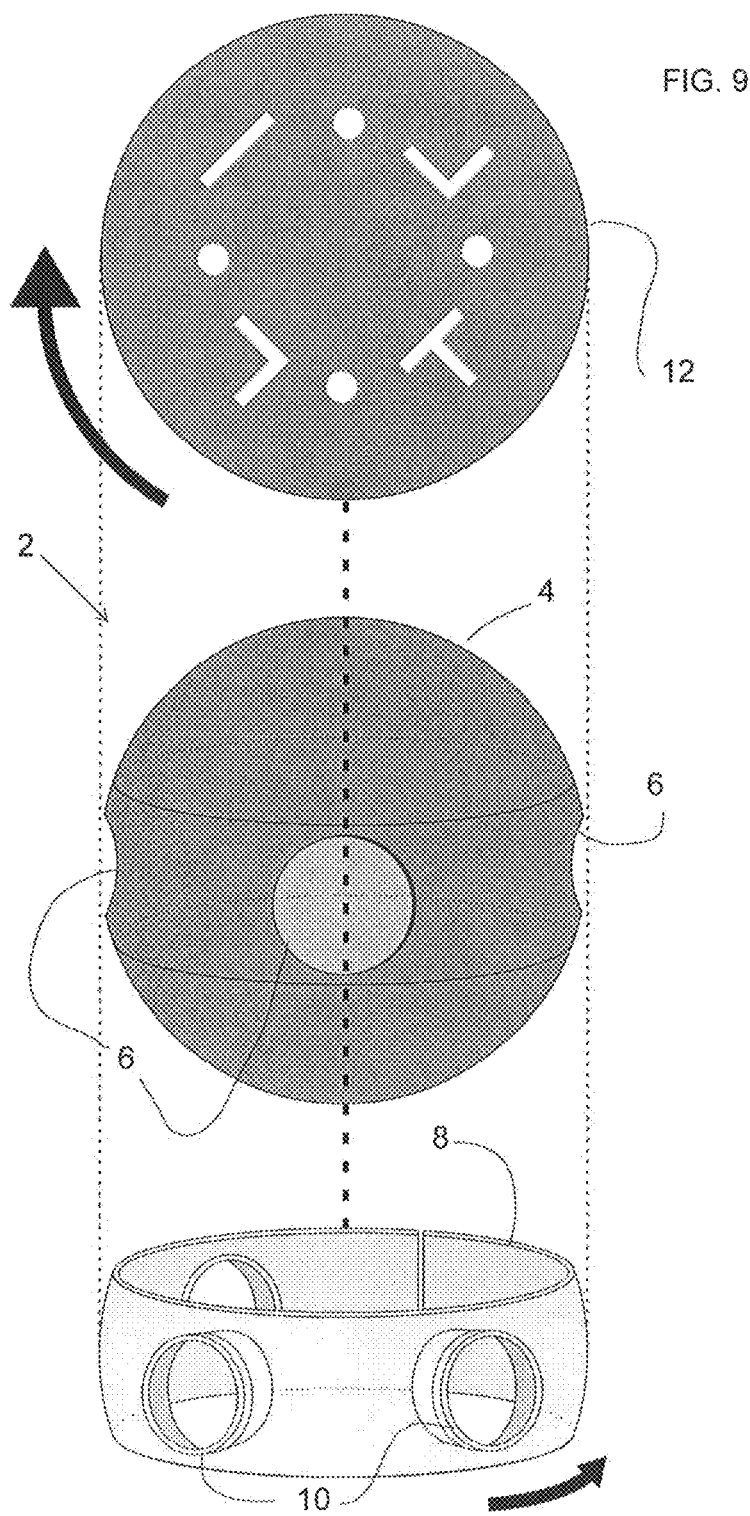
FIG. 9 is an exploded view of the medical stopcock of FIG. 1 in a fourth stable closed position, 90 degrees from the third stable closed position and 45 degrees from the fourth stable open position, where all there external ports on the outer collar are closed, off from all of the through holes in the hollow sphere.
Figure 10:
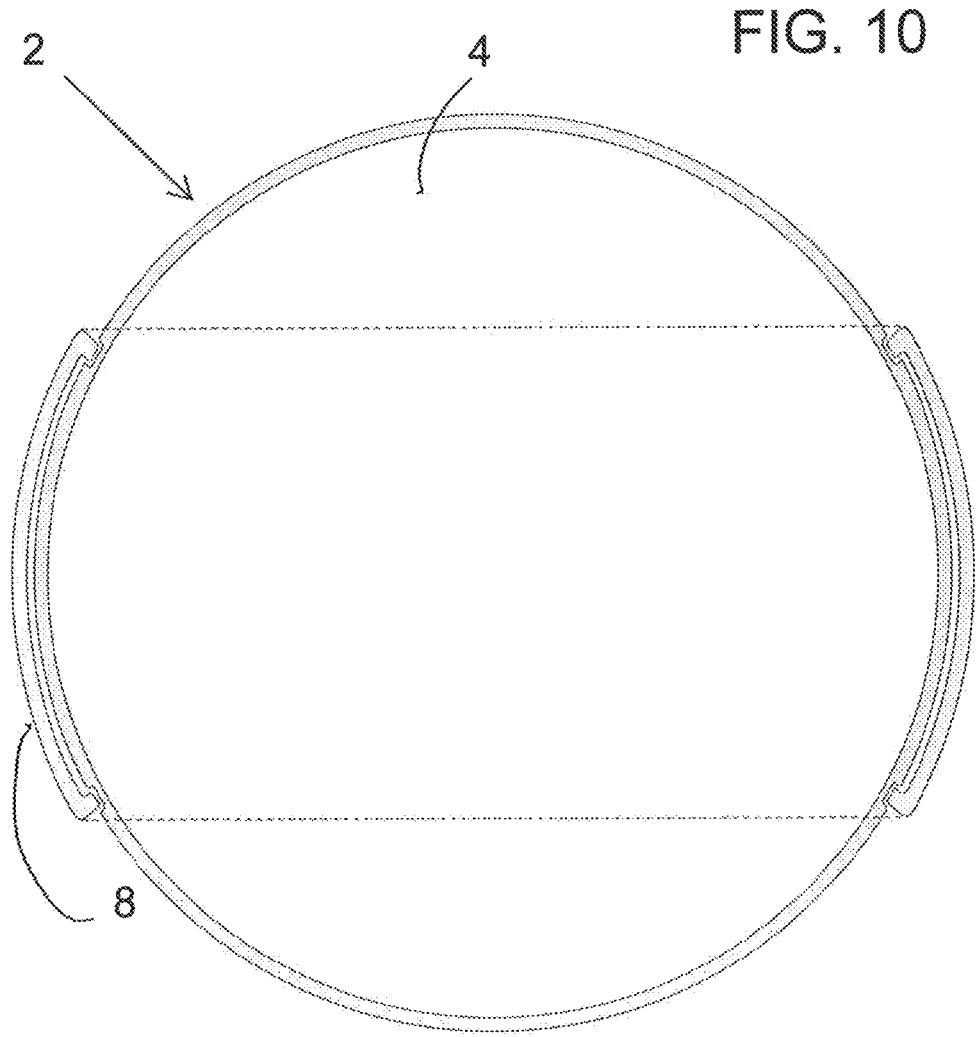
FIG. 10 is a vertical cross section of the medical stopcock of FIG. 1 along a plane that does not intersect any through holes or external ports.
Figure 11:
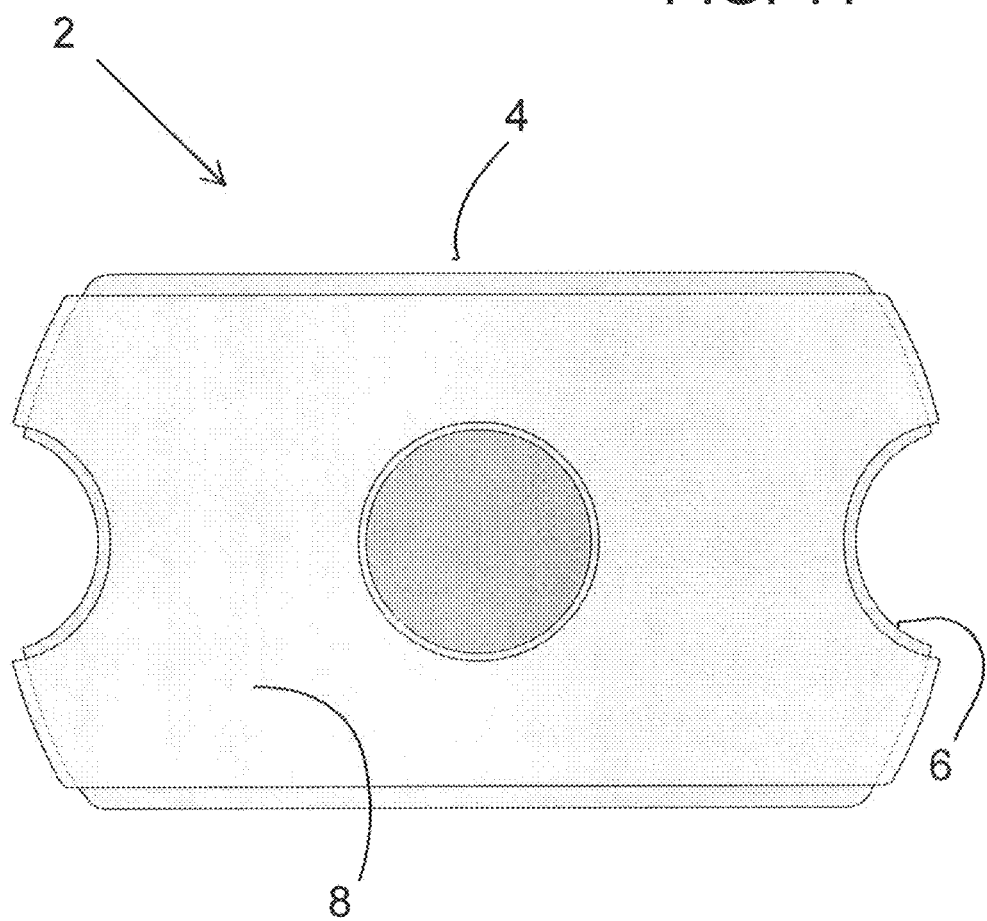
FIG. 11 is a is a front view of a second embodiment of the medical stopcock where the hollow sphere is shaped as an oblate spheroid with a flat top and bottom and the external ports on the outer collar are not shown for clarity.

The present invention will be understood by reference to the following detailed description, which should be read in conjunction with the appended drawings. It is to be appreciated that the following detailed description of various embodiments is by way of example only and is not meant to limit, in any way, the scope of the present invention.

Turning now to FIGS. 1-20, a brief description concerning the various components of the present invention will now be briefly discussed. As can be seen in these embodiments, there are several design methods that can be done to optimize medical stopcocks according to the disclosed invention.

In a first embodiment, the medical stopcock 2 has a smoother surface in a spherical shape. The newly designed stopcock 2 should ideally eliminate the pointed edges present in the medical stopcocks currently known in the art (the lever or the open/stop handle) from the design.

A 3-way stopcock currently known in the art has a solid cylindrical rod that is inserted perpendicular and at the intersection of the "T intersection" of the ports. This rod has a lever at the end of it to allow it to rotate. The rod also has boreholes perpendicularly through it. In a 3-way stopcock these would mirror the three-access port. They would be narrower than them. When the rod is rotated so that they perfectly mirror the access ports a flow of all three tributaries is allowed. The rod can be rotated so that all three, two, one or no ports are open.

In one embodiment of the medical stopcock 2 disclosed, the internal rod and lever system is eliminated. It could be said to allow for an inverse arrangement of the stopcock 2 parts.

One embodiment of this improved stopcock 2 consists of a hollow sphere 4 with three through holes 6 of preferably equal diameter at 90 degree intervals. An outer ring 8 with the external ports 10 is placed around the hollow sphere perimeter. The outer ring 8 can be rotated around the hollow sphere 4, or, conversely, the hollow sphere 4 can be rotated within the outer ring 8. The external ports 10 can be rotated with the outer ring 8 as shown in FIGS. 2-9 to allow for all three external ports 10 to open or closed as needed. When an external port 10 is rotationally aligned with a through hole 6, a fluid connection is established between the external port 10 and the interior of the hollow sphere 4 and the external port 10 can be considered open or on. When an external port 10 is fully rotationally spaced from any through hole 6, the external port is fluidly isolated from the interior of the hollow sphere 4 and the external port 10 can be considered closed or off.

There is no limit to the type of external port 10 that can be added to the outer ring 8. These can be a standard tubing input, leer lock, injection port or another standard or newly invented port.

The external ports 10 and holes 6 that match them can be in a plurality of numbers and a plurality of angels separating them so that they continue to function as a proper medical stopcock 2 valve.

There are no limits to the material that may be used to construct this valve 2. A range of plastics and polymers both hard and soft can be used as long as the resulting valve 2 is structurally stable.

Figure 12:
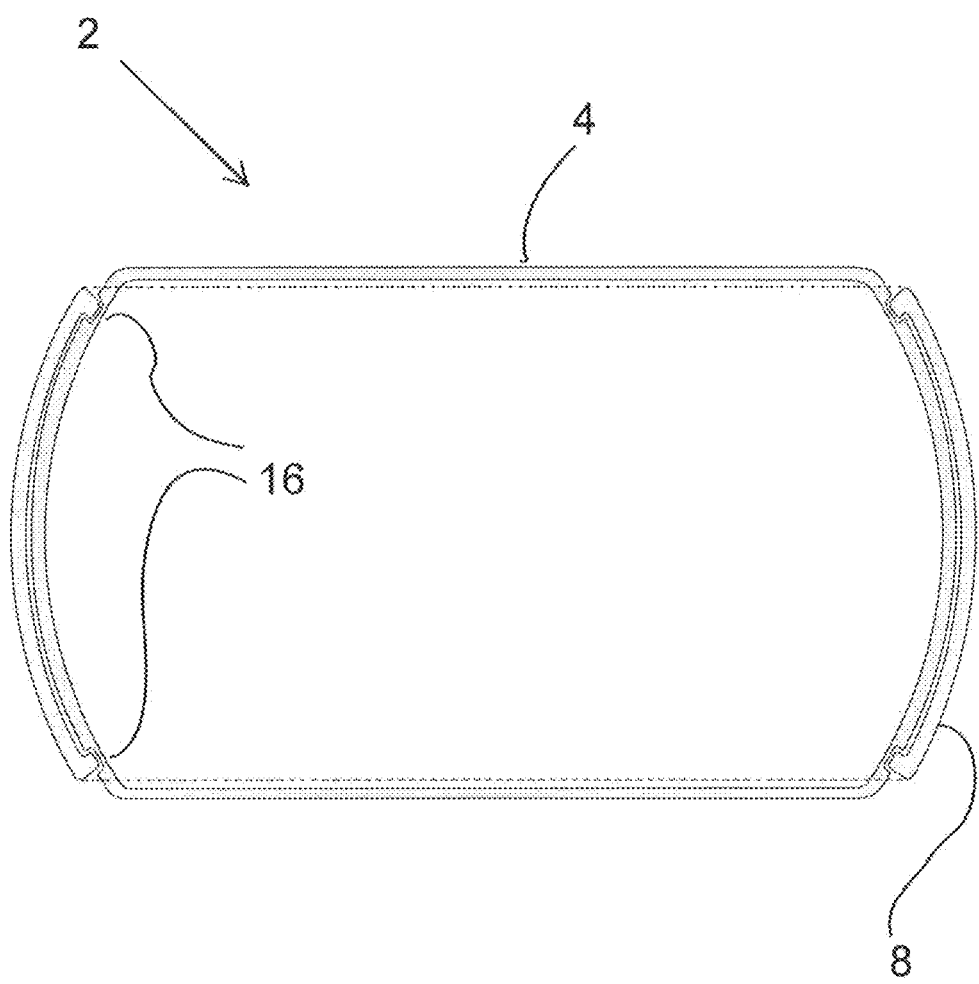
FIG. 12 is a vertical cross section of the medical stopcock of FIG. 11 along a plane that does not intersect any through holes or external ports.
Figure 13:
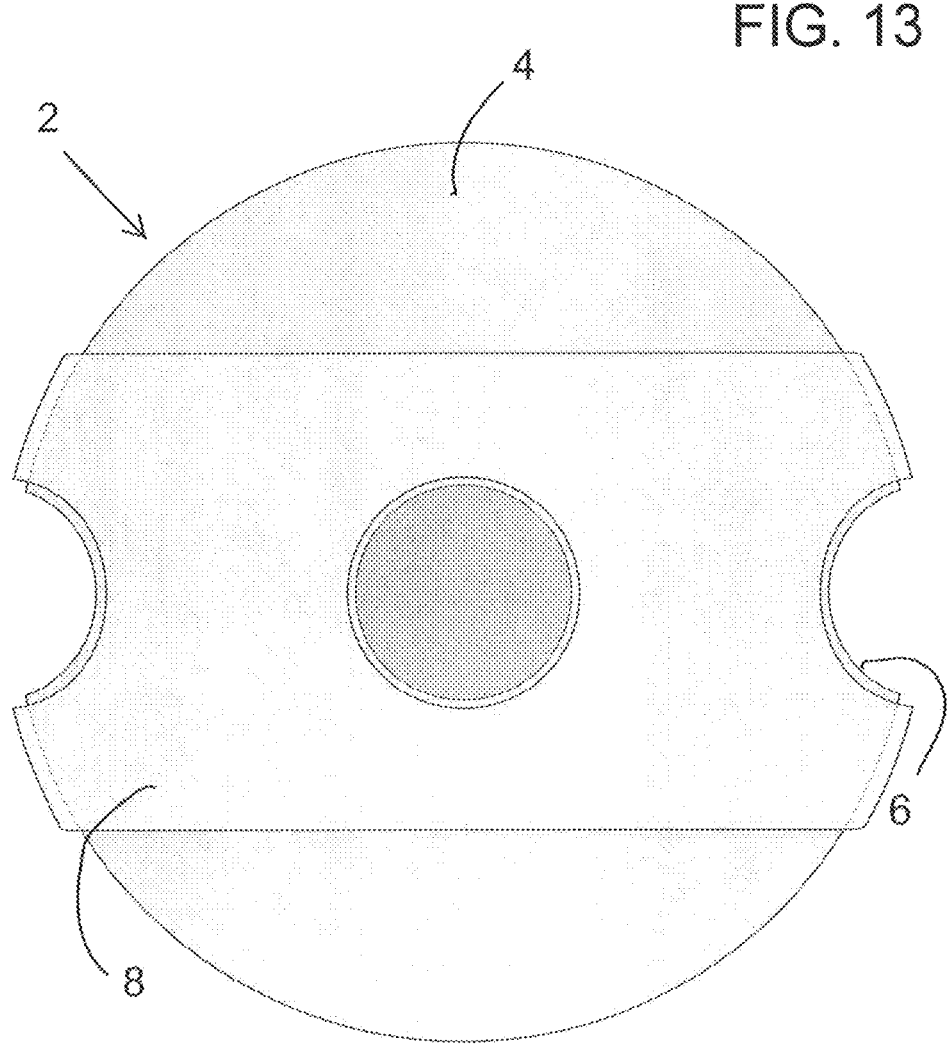
FIG. 13 is a front view of the medical stopcock of FIG. 1 with the external ports on the outer collar not shown for clarity.
Figure 14:
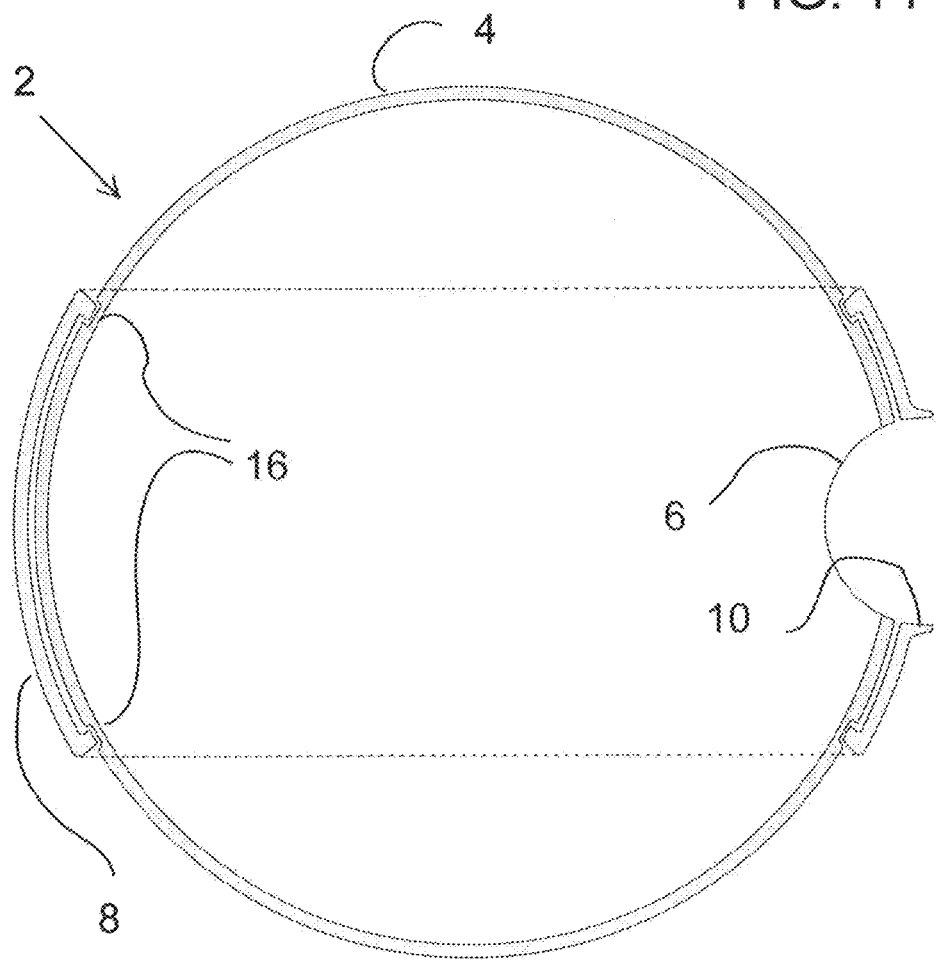
FIG. 14 is a vertical cross section of the medical stopcock of FIG. 1 along a plane that intersects a single through hole and a single external port.
Figure 15:
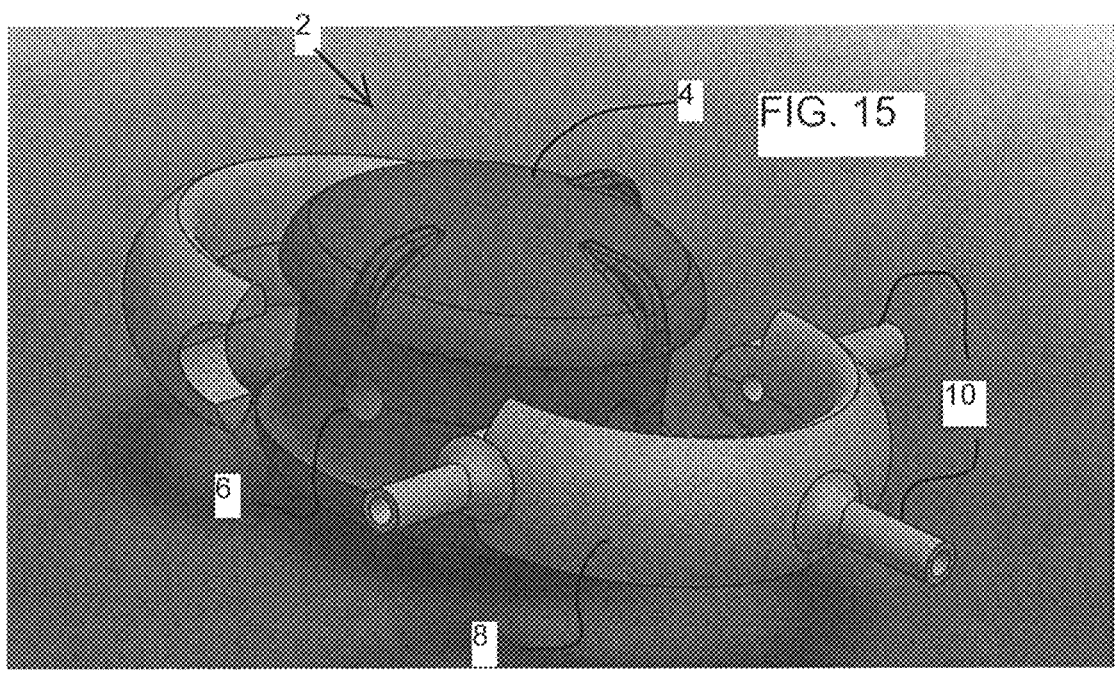
FIG. 15 is a partially exploded view of a third embodiment of the medical stopcock with an oblate spheroid shape, a concave channel along the perimeter of the hollow sphere, and three exterior through hole identifiers on the top of the hollow sphere, each radially aligned with a respective through hole.
Figure 16:
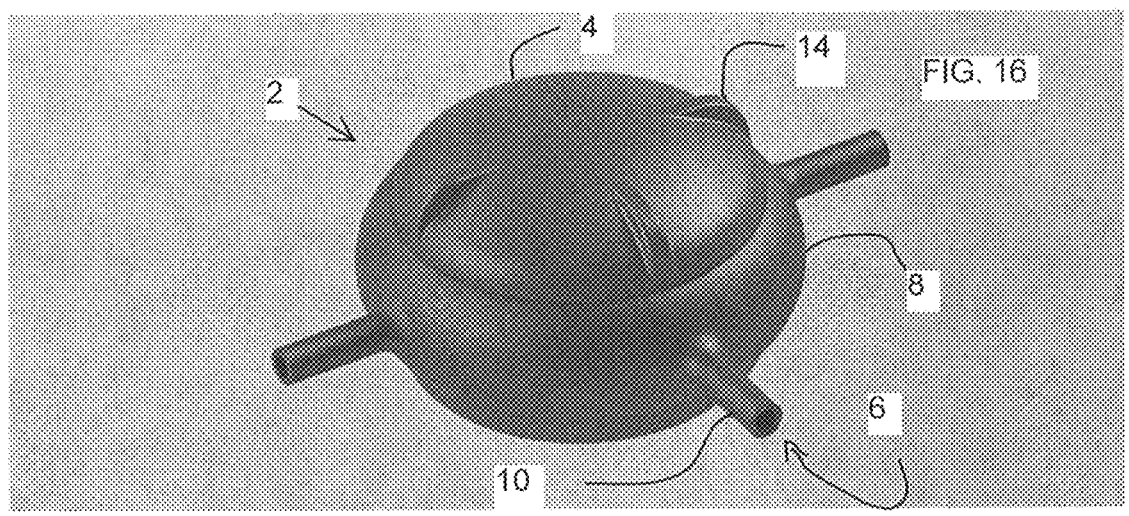
FIGS. 16 and 17 are isometric views of a variation of the medical stopcock of FIG. 15.
Figure 17:
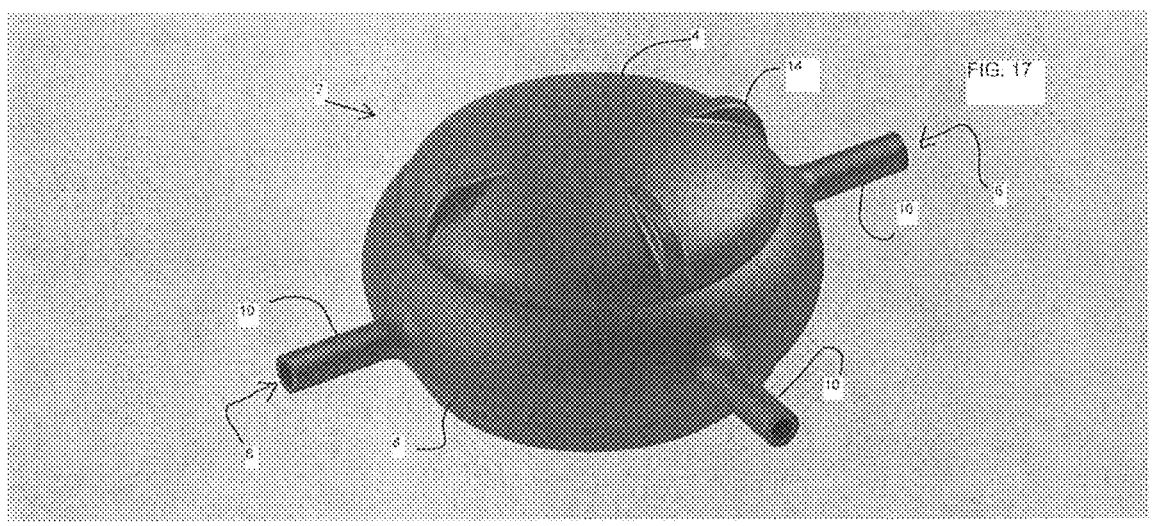
Figure 18:
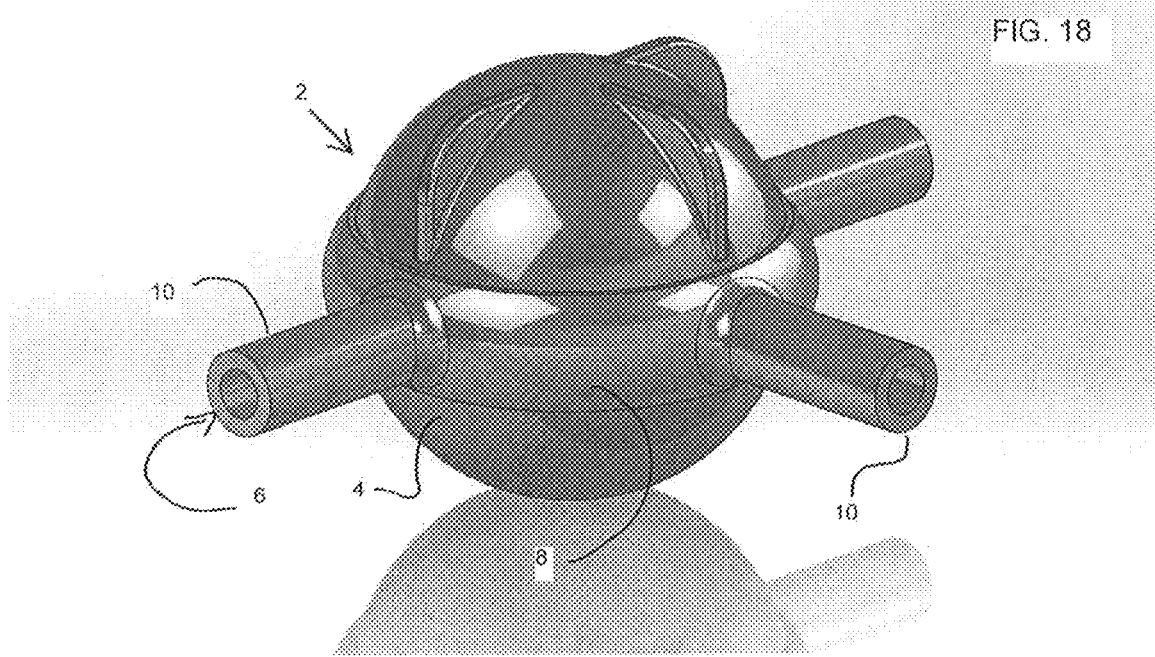
FIG. 18 is an isometric views of a variation of the medical stopcock of FIG. 1 that also includes three exterior through hole identifiers on the top of the hollow sphere, each radially aligned with a respective through hole.
Figure 19:
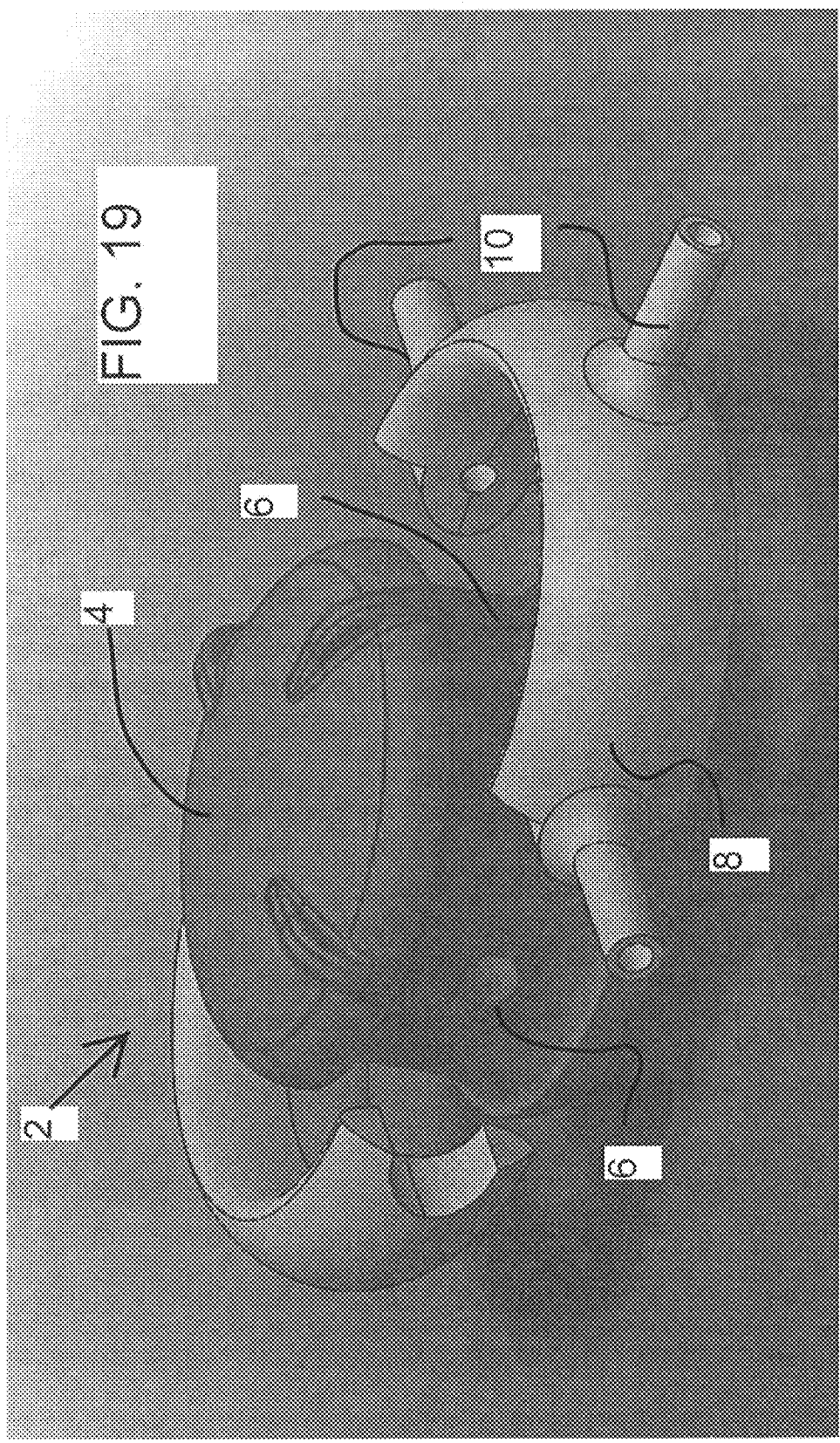
FIG. 19 is an additional partially exploded view of the medical stopcock of FIG. 15.
Figure 20:
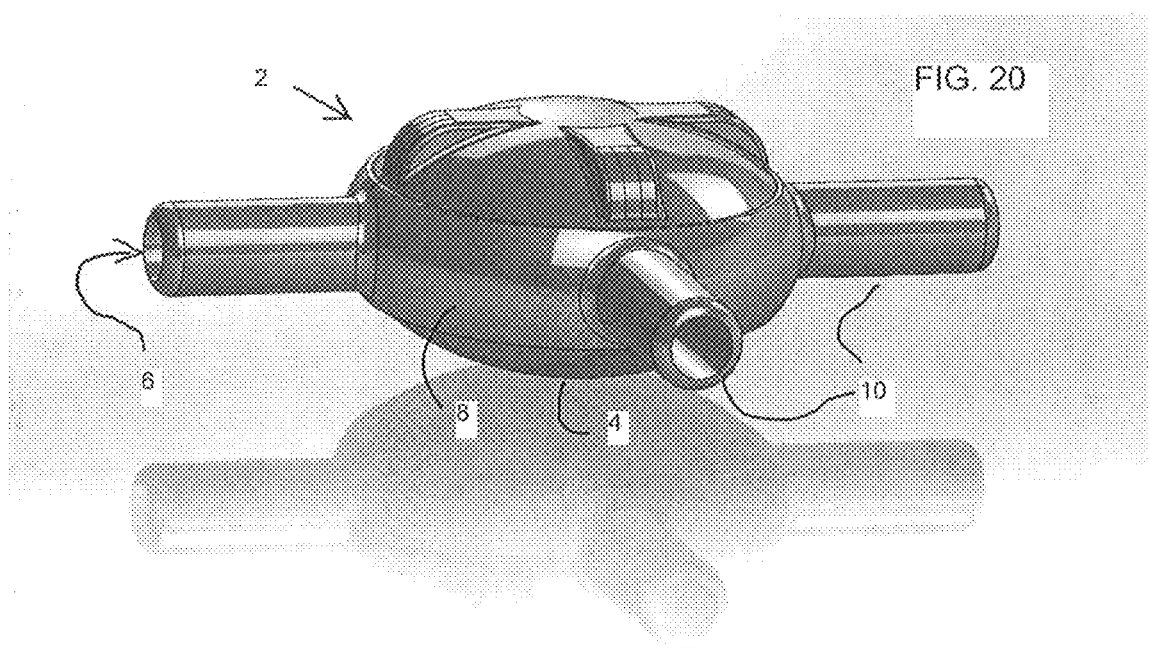
FIG. 20 is an isometric views of a variation of the medical stopcock of FIG. 11 that also includes three exterior through hole identifiers on the top of the hollow sphere, each radially aligned with a respective through hole.

As shown in FIGS. 12 and 14, a track 16 can connect the hollow sphere 4 to the outer ring 8 and provide a pressurized seal. A rubber or other material "o-ring" to act as a pressure seal may be sandwiched between the hollow sphere 4 and the outer ring 8 with external ports 10. This o-ring or track 16 would preferably have holes that appropriately track the rotation of the device.

The hollow sphere 4 portion of this valve 2 would act to eliminate constriction points that stop flow and allow bacteria to accumulate. The elimination of the rod and lever would also prevent ulcers or patient discomfort as well as accidental turning of the valve.

The hollow sphere 4 component could be flattened to an oblate spheroid or to that of a hollow circle that has an appropriate diameter for rotation of the outer ring 8.

Another embodiment does not require that the hollow sphere 4 be fully hollow. A tributary could be constructed to continuously flow through the hollow sphere 4.

Another embodiment could use a standard 3-way stopcock 2 "T-intersection arrangement" to allow for flow to continue through the hollow sphere 4 portion.

One or more additional side ports or through boles 6 (not shown), such as an aspiration port, can be placed on the top of the hollow sphere 4, spaced from the outer ring 8. The additional side port would be in a non-rotating position. Other non-rotating positions (side ports) can be installed to the hollow sphere 4 and be used for aspirating, fluid sampling, or administration of medications. These additional side ports may be selectively closeable, via a cap or other such closures, may be initially open, or may be initially sealed and have membranes or surfaces that are designed to be perforated when access is desired.

The size of this valve can be scaled up or down. A scaled up version of this device could be used for dialysis, heart pump machines or other medical applications.

As shown in FIGS. 2-9, on the surface of the hollow sphere, there can be a flow path indicator 12 that shows which external ports 10 are fluidly connected to the interior of the hollow sphere 4 with a given relative rotation of the hollow sphere 4 and the outer collar 8. This embodiment of the device has marking that clearly show the 8 possible on/off positions of a three-way port embodiment. This eliminates the confusion of the older technology in the art with a single "off position," In the older versions once the valve is not in a complete open position there may be constricted flow. The disclosed embodiment eliminates that issue by having clear markings on the fully open (on) positions as well as the fully closed (off) positions.

Additionally or alternatively, as shown in FIGS. 15-20 exterior through hole identifiers 14 can be located on the surface of the hollow sphere. The exterior through hole identifiers 14 would be radially aligned with a through hole 6, and could be a raised bump or curved edge, or could simply be a visual marking identifying the location of each through hole 6. Though in one embodiment the outer ring 8 may turn smoothly around the hollow sphere 4 without obstruction, it is anticipated that there will be a number of stable on or open positions where the at least one through hole 6 is circumferentially aligned with at least one external port 10, and a number stable off of closed positions where all through holes are circumferentially spaced from any external port 10. Indentations, catches, groves (not shown) in the surface of the outer ring 8 and the hollow sphere 4 interact with one another to provide tactile feedback when a stable position is reached. Other methods of such tactile feedback know in the art are also included in this invention. In between the stable positions, it is anticipated that the outer ring 8 will slide freely around the perimeter of the hollow sphere 4 until it encounters another stable position.

Other aspects and advantages will become apparent upon consideration of the foregoing detailed description and the attached drawings, in which like elements are assigned like reference numerals.

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

Wherefore we claim:
1. A medical stopcock valve comprising:
a hollow body having a plurality of through holes around a perimeter of the hollow body;
an outer ring encapsulating the perimeter, the outer ring having a plurality of external ports;
the outer ring being rotatable around the perimeter to open and close access between the external ports and the through holes;
at least three through hole;
at least three exterior ports;
eight possible stable on/off positions of the outer ring as the outer ring rotates around the perimeter; and
eight unstable intermediate positions between the stable on/off positions.

2. The medical stopcock of claim 1 wherein there are one of three, four, and five through holes.

3. The medical stopcock of claim 1 wherein there are an equal number of external ports as through holes.

4. The medical stopcock of claim 1 wherein the hollow body is substantially a sphere shape.

5. The medical stopcock of claim 1 wherein the hollow body is substantially one of an oblate spheroid shape and a prolate spheroid shape.

6. The medical stopcock of claim 1 wherein the through holes are spaced equidistant from one another.

7. The medical stopcock of claim 1 wherein each through hole is spaced $360/(x+1)$ degrees from at least one adjacent through hole, where x is equal to the number of through holes.

8. The medical stopcock of claim 1 wherein the outer ring, by rotating around the hollow body, has multiple stable closed positions, where no fluid may enter or leave the hollow body, and has at least one all open position where all the through holes are aligned with an external port.

9. The medical stopcock of claim 1 wherein any two through holes may be selectively aligned with a respective external port while any remaining through holes are closed off from external ports.

10. The medical stopcock of claim 1 wherein no rod or lever is present.

11. The medical stopcock of claim 1 wherein a diameter of the hollow body is between 1.5 and 3.5 times a height of the outer ring.

12. The medical stopcock of claim 1 further comprising a plurality of selectively closeable additional through holes, wherein the additional through holes are spaced from the outer ring.

13. The medical stopcock of claim 1 further comprising a selectively closeable additional through hole, wherein the additional through hole is located at a top of the hollow body and is spaced from the outer ring.

14. The medical stopcock of claim 1 wherein one of tactile feedback and auditory feedback is provided when the outer ring is rotated into a stable on or a stable off position.

15. A medical stopcock valve comprising:
   a hollow body having three through holes around a perimeter of the hollow body;
   the through holes are all along a common plane and each through hole is spaced ninety degrees from at least one adjacent through hole;
   an outer ring encapsulating the perimeter, the outer ring being fluid tightly connected to the hollow body and having three external ports;
   the outer ring being fully rotatable around the perimeter to open and close access between the external ports and the through holes;
   the outer ring, by rotating around the hollow body, has multiple stable closed positions, where no fluid may enter or leave the hollow body, and has at least one all open position where all the through holes are aligned with an external port;
   any two through holes may be selectively aligned with a respective external port while any remaining through holes are closed off from external ports;
   no rod or lever is present;
   a diameter of the hollow body is between 1.5 and 3.5 times a height of the outer ring;
   at least one selectively closeable additional through hole is located on a top of the hollow body and is spaced from the outer ring;
   the outer ring having at least eight possible stable on/off positions as the outer ring rotates around the perimeter,
   the outer ring having at least eight unstable intermediate positions between the stable on/off positions, the outer ring requiring more force to rotate out of a stable position than through an unstable position; and
   one of tactile feedback and auditory feedback is provided when the outer ring is rotated into a stable on position or a stable off position.

* * * * *